United States Patent [19]

Foss

[11] Patent Number: 4,762,426
[45] Date of Patent: Aug. 9, 1988

[54] REMOTE PASSIVE TEMPERATURE SENSOR

[75] Inventor: Norman A. Foss, North Oaks, Minn.

[73] Assignee: Honeywell Inc., Minneapolis, Minn.

[21] Appl. No.: 943,418

[22] Filed: Dec. 19, 1986

[51] Int. Cl.$^4$ .................. G01J 5/08; G01W 1/00; G02B 5/124; G02B 26/08

[52] U.S. Cl. ........................ 374/130; 73/335; 73/337; 250/231 R; 350/102; 350/487

[58] Field of Search ............... 374/18, 19, 130, 131, 374/205; 350/102, 103, 359, 360, 487; 340/584, 594, 600, 602; 250/231 R, 338 R, 353; 73/29, 73, 335–337; 357/55; 356/43

[56] References Cited

U.S. PATENT DOCUMENTS

| | | | |
|---|---|---|---|
| 3,374,044 | 3/1968 | Benson | 350/102 |
| 3,850,038 | 11/1974 | Thoma et al. | 374/205 |
| 4,204,742 | 5/1980 | Johnson et al. | 350/487 |
| 4,224,608 | 9/1980 | Lederer | 340/556 |
| 4,234,245 | 11/1980 | Toda et al. | 350/269 |
| 4,472,239 | 9/1984 | Johnson et al. | 357/55 |
| 4,672,199 | 6/1987 | Anderson et al. | 250/227 |
| 4,682,503 | 7/1987 | Higashi et al. | 357/55 |
| 4,730,109 | 3/1988 | Afromowitz | 250/231 R |

FOREIGN PATENT DOCUMENTS 80021 6/1980 Japan .............. 250/231 R

Primary Examiner—William A. Cuchlinski, Jr.
Assistant Examiner—W. Morris Worth
Attorney, Agent, or Firm—Omund R. Dahle

[57] ABSTRACT

A remote passive condition sensor apparatus such as a temperature or humidity sensor apparatus. A corner cube reflector at a remote location, where it is not feasible to have electrical connections or batteries, receives and reflects back radiant energy to an optical readout instrument. Condition responsive elements in the corner reflector affect the amount of reflected radiant energy as a function of the condition sensed.

12 Claims, 1 Drawing Sheet

REMOTE PASSIVE TEMPERATURE SENSOR

BACKGROUND AND SUMMARY OF THE INVENTION

This invention is directed to a remote passive condition sensor such as a temperature or humidity sensor. The invention is of an optical type having no electrical connection or source to a remotely located completely passive sensor.

In the prior art there has been used remotely located sensors with electrical connections extended thereto from a site where readout is desired. Other remote sensors have been electrically powered by batteries or the like and utilize radio transmission to a readout station.

The present invention described herein utilizes temperature or humidity sensors which require no electrical circuitry whatsoever and are read out by simple optical techniques to permit low cost sensing in remote or inaccessible areas.

DESCRIPTION

Figure 1:
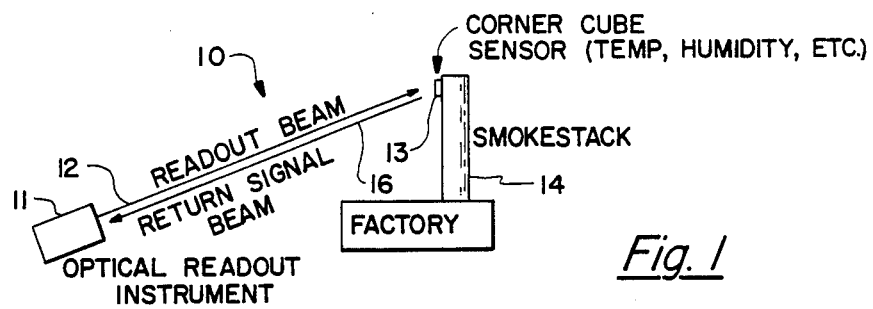
FIG. 1 is a system sketch of a typical installation of the invention.

Referring now to FIG. 1, there is shown an overview of the non-electrical, optically read sensor system 10 in which an observer accessible optical readout instrument 11 comprises an optical interrogator. The optical interrogator consists preferably of a dual wavelength light source 12 which is directed towards a sensor means 13 located at a generally inaccessible location such as the top of a smokestack 14. The sensor means is completely passive having no electrical connections thereto and no electrical source. The sensor means is optical in nature and is in the form of a corner cube reflector 15 (FIG. 2), i.e. a retroreflector. This corner cube reflector 15 is one which returns a light beam, such as beam 12 in the direction of its source. This return signal beam in FIG. 1 has been shown as beam 16. The corner cube reflector 15 comprises three reflecting surfaces 20, 21 and 22 each of which is at right angles to the other two. From this construction the result is obtained that no matter how the reflector is tilted, so long as the radiant beam enters the solid angle formed by the three reflecting surfaces, the light is reflected back towards the source. The return signal beam 16 returns to the optical readout instrument 11 for detection by a sensor therein.

Figure 2:
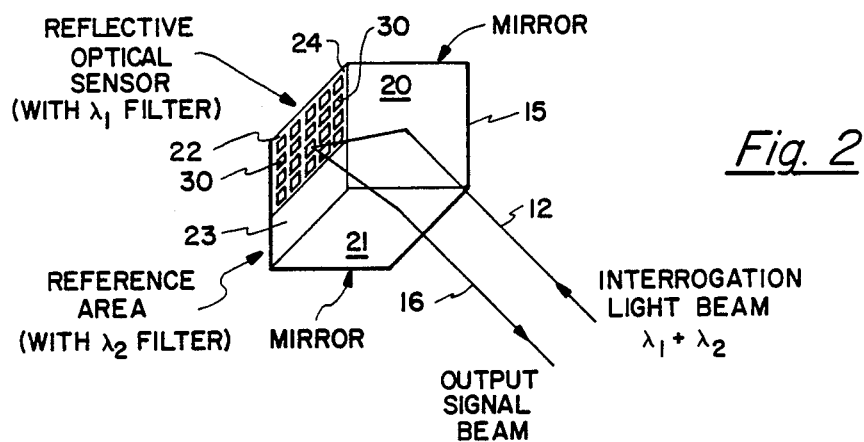
FIG. 2 is an enlargement of a portion of FIG. 1.

Referring to FIG. 2, the incoming interrogation light beam 12 has preferably a component $\lambda_1$ and a component $\lambda_2$. The reflecting surfaces 20 and 21 are mirror surfaces. The reflecting surface 22 which may be a wafer of silicon has a reflective reference area 23 with a $\lambda_2$ filter, and a reflective optical sensor area 24 with a $\lambda_1$ filter. The sensor area 24 is coated with a layer 25 of silicon nitride. The thickness may be on the order of 5000–10,000 Å, for example. The reflective characteristics of the sensor area 24 are modified by condition responsive microstructure sensor elements 30 which are formed in the silicon nitride face. As the sensor temperature (or humidity for humidity sensor) changes, the reflectance of the corner cube changes such that the measured reflectance is then functionally related to the sensor temperature. To avoid absolute calibration problems of the reflectance caused by fogging or dirt on the corner cube, the cube contains the reference region 23 which is spectrally filtered from the temperature sensor region 24 such that it can be used as a reference reflector on the cube sensor. To increase reflectivity the silicon reference area 23 can be coated with a multilayer dielectric like aluminum oxide or silicon dioxide, for example. This multilayer can also be tuned to the wavelength $\lambda_2$ so that it also acts as the $\lambda_2$ filter.

Figure 3:
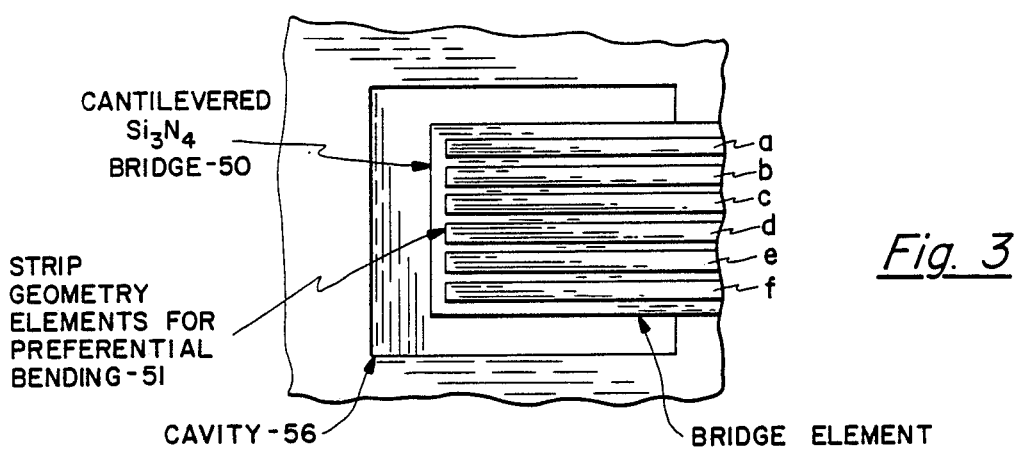
FIG. 3 is a top view and FIG. 4 is a cross sectional view of the detail of one single element of the optical readout sensor.
Figure 4:
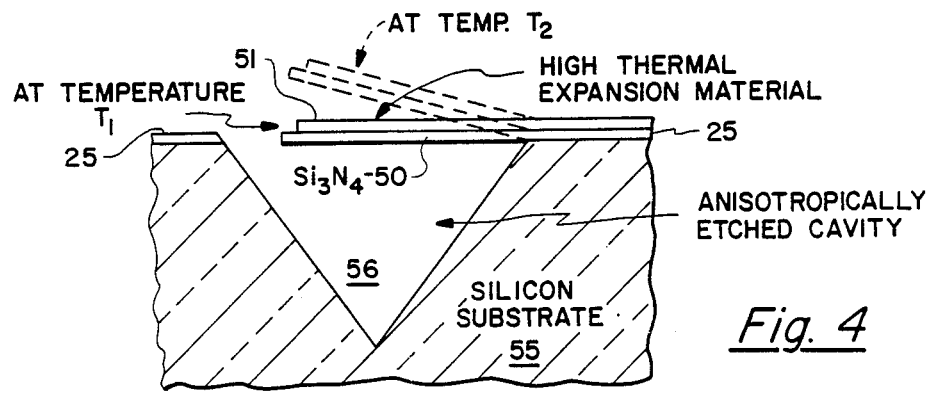

FIGS. 3 and 4 show the detail of one single element 30 of the optical readout sensor utilized in the implementation of the corner cube reflector. In FIG. 4 a $Si_3N_4$ cantilever 50 has coated thereon in strips a layer of higher thermal expansion material 51 such as by sputtering or ion beam deposition. The higher thermal expansion material 51 may be, for example, the material aluminum or platinum and of the same order of thickness as the $Si_3N_4$ layer 25. For a humidity responsive sensor, the high humidity expansion material 51 may be, for example, the material polyimide. Layer 51 is applied to the layer of $Si_3N_4$ before the cantilevers are formed. Thus the cantilevered bilevel film consists of two different materials which have different thermal temperature expansion coefficients (or in the case of a humidity, different moisture expansion coefficients). The coated cantilever acts like a thermally responsive bimetal and bends upwardly or downwardly with changing temperature. FIG. 4 shows a first position of the cantilever at a temperature $T_1$ and shows a second position of the cantilever at a temperature $T_2$. This change in angle of the numerous microsensors 30 on the corner cube then deflects more or less of the return radiation away from the local ground instrument 11.

A silicon substrate 55, to which the $Si_3N_4$ layer is grown, has an anisotropically etched cavity 56 beneath the cantilever 50. Details of fabricating microstructure cantilevers of $Si_3N_4$ over cavities in a silicon substrate similar to these can be found in U.S. Pat. No. 4,472,239, assigned to the same assignee as the present invention, and the teachings are incorporated by reference. Briefly however a monocrystalline silicon substrate body 55 has its surface covered with a dielectric layer 25, such as silicon nitride which is typically 3000 to 10,000 angstroms thick. Openings are then etched through the $Si_3N_4$ to delineate the cantilever structure 50 shown in FIGS. 3 and 4. Strip geometry elements 51, shown as a,b,c,d,e,f, (FIG. 3) are preferred for causing preferential bending of the cantilevered $Si_3N_4$ bridge. An anisotropic etchant that does not attack the silicon nitride is used to etch out silicon in a controlled manner from beneath the cantilever structures leaving a cavity 56 (KOH plus isopropyl alcohol is a suitable etchant). Since the surface of the silicon nitride layer 50 of region 24 may not be as good a reflector as the silicon, it may be desirable to coat the surface with 100 Å of aluminum, for example, to increase the reflectability.

The embodiments of the invention in which an exclusive property of right is claimed are defined as follows:

1. A non-electrical, optically read condition sensor apparatus for determining the condition at a remote location by transmitting a radiant energy beam to the remote location and measuring a reflected return beam, the apparatus comprising in combination:

a local ground instrument comprising;
      means for generating an interrogation beam of radiant energy;

means directing said interrogation beam to a remotely located corner-cube sensor; and,
return radiation sensing means for sensing the intensity of the reflected returned beam;
a passive, unpowered, remotely located corner cube sensor means comprising;
a reflective corner cube having a plurality of adjoining reflective faces at right angles to each other;
a condition sensing area on one of said reflective corner cube faces, said sensing area including condition responsive bi-level film cantilever member means forming a part of said condition sensing area, said bi-level film cantilever member means consisting of two different materials which have different expansion coefficients whereupon as the condition changes the bi-level film cantilever member means bends to a degree dependent on the amount of change of the condition sensed and thus deflects more or less of the return radiation away from the local ground instrument.

2. A non-electrical, optically read condition sensor apparatus for determining the condition at a remote location, the apparatus comprising in combination:
a local ground instrument comprising;
means for generating an interrogation beam of radiant energy having a component $\lambda_1$ and a component $\lambda_2$;
means directing said interrogation beam to a remotely located corner-cube sensor; and,
return radiation sensing means for sensing the intensity of returned $\lambda_1$ and $\lambda_2$ components;
a passive, unpowered, remotely located corner cube sensor means comprising;
a reflective corner cube having three adjoining faces at right angles to each other;
a reference area on one of said corner cube faces;
$\lambda_2$ filter means associated with said reference area of said corner cube for returning said $\lambda_2$ component to said local ground instrument without modification;
a condition sensing area on said one of said reflective corner cube faces; $\lambda_1$ filter means associated with said condition sensing area, said sensing area including condition responsive bi-level film cantilever member means forming a part of said one of said reflective corner cube faces, said bi-level film consisting of two different materials which have different expansion coefficients whereupon as said condition changes, the bi-level film cantilever member means bends to a degree dependent on said condition, and thus deflects more or less of the $\lambda_1$ return radiation.

3. A non-electrical, optically read temperature sensor apparatus for determining the temperature at a remote location, the apparatus comprising in combination:
a local ground instrument comprising;
means for generating an interrogation beam of radiant energy having a component $\lambda_1$ and a component $\lambda_2$;
means directing said interrogation beam to a remotely located corner-cube sensor; and,
return radiation sensing means for sensing the intensity of returned $\lambda_1$ and $\lambda_2$ components;
a passive, unpowered, remotely located corner cube sensor means comprising;
a reflective corner cube having three adjoining faces at right angles to each other;
a reference area on one face of said corner cube;
$\lambda_2$ filter means associated with said reference area of said corner cube for returning said $\lambda_2$ component to said local ground instrument without modification;
a temperature sensing area of said reflective corner cube, said sensing area including temperature responsive bi-level film cantilever member means forming a part of said one face, said bi-level film consisting of two different materials which have different thermal expansion coefficients whereupon as temperature changes the bi-level film cantilever member means bends to a degree dependent on absolute temperature and thus deflects more or less of the return radiation.

4. A passive condition responsive corner cube reflector means comprising:
a reflective corner cube having a plurality of adjoining reflective faces at right angles to each other,
at least one of said reflective faces comprising:
a wafer of single crystalline silicon having a planar surface coated with a thin film layer of reflective silicon nitride;
a plurality of silicon-nitride cantilever member means formed in said silicon nitride layer, said cantilever member means having etched cavities in the silicon beneath them, said silicon nitride having a first expansion coefficient;
a layer of material of a different expansion coefficient coated on said cantilever member means so that at a first sensed condition said coated cantilever member means are in the plane of said thin film layer of reflective silicon nitride and at a second sensed condition said coated cantilever member means are warped out of said plane by an amount which is a function of said second sensed condition.

5. The corner cube reflector means according to claim 4 in which said first and second sensed condition are temperature.

6. The corner cube reflector means according to claim 4 in which said first and second sensed condition are humidity.

7. The condition sensor apparatus according to claim 1 in which the condition responsive bi-level film cantilever member means are responsive to humidity.

8. The sensor apparatus according to claim 3 in which the temperature sensing area of said reflective corner cube includes $\lambda_1$ filter means associated therewith for passing and returning said $\lambda_1$ component to said local ground instrument.

9. The sensor apparatus according to claim 3 in which said bi-level film consists of a first layer of silicon nitride and a second layer selected from a group consisting of aluminum and platinum.

10. The condition sensor apparatus according to claim 7 in which said bi-level film cantilever member means has one material consisting of a layer of silicon nitride and the other material consisting of a layer of polyimide.

11. The corner cube reflector means according to claim 5 in which the layer of material of said different expansion coefficient is selected from a group consisting of aluminum and platinum.

12. The corner cube reflector means according to claim 6 in which the layer of material of said different expansion coefficient consists of a layer of polyimide.

* * * * *